US008767911B2

(12) United States Patent
Ren et al.

(10) Patent No.: US 8,767,911 B2
(45) Date of Patent: Jul. 1, 2014

(54) TOMOSYNTHESIS WITH SHIFTING FOCAL SPOT AND OSCILLATING COLLIMATOR BLADES

(71) Applicant: Hologic, Inc., Bedford, MA (US)

(72) Inventors: Baorui Ren, Andover, MA (US); Andrew P Smith, Lexington, MA (US); Thomas Farbizio, Patterson, NY (US); Zhenxue Jing, Chadds Ford, PA (US); Jay Stein, Boston, MA (US)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 13/966,606

(22) Filed: Aug. 14, 2013

(65) Prior Publication Data
US 2014/0016737 A1    Jan. 16, 2014

Related U.S. Application Data

(63) Continuation of application No. 12/849,294, filed on Aug. 3, 2010, now Pat. No. 8,515,005, which is a continuation-in-part of application No. 12/623,472, filed on Nov. 23, 2009, now Pat. No. 8,457,282.

(60) Provisional application No. 61/117,453, filed on Nov. 24, 2008.

(51) Int. Cl.
G01N 23/083    (2006.01)
G21K 1/02      (2006.01)
H05G 1/52      (2006.01)
H05G 1/02      (2006.01)

(52) U.S. Cl.
USPC ............................. 378/22; 378/147

(58) Field of Classification Search
USPC ............ 378/21–23, 26, 37, 91, 93, 111, 112, 378/125, 126, 137, 145–147, 150, 151, 204, 378/205, 210, 901
See application file for complete search history.

(56) References Cited

U.S. PATENT DOCUMENTS 5,274,690 A   12/1993   Burke
5,313,510 A    5/1994   Ebersberger (Continued)

FOREIGN PATENT DOCUMENTS

EP    1028451      8/2000
WO    WO9803115    1/1998

(Continued)

OTHER PUBLICATIONS

International Search Report and Written Opinion from related PCT application PCT/US09/065451 dated Feb. 5, 2010.

(Continued)

Primary Examiner — Anastasia Midkiff

(57) ABSTRACT

In a tomosynthesis system a static focal spot is moved in a direction opposite to and generally synchronized with the directional movement of an x-ray source and X-ray collimator blades are moved during each exposure in synchronization with the shifting of the static focal spot. The synchronized movement of the static focal spot, x-ray tube and collimator blades helps keep the effective focal spot fixed in space relative to the breast, detector or both during the entire duration of the exposure and keeps the x-ray field on the detector and breast static. The shifting collimator blades follow an oscillating pattern over the multiple x-ray exposures of a tomosynthesis scan.

19 Claims, 5 Drawing Sheets

(56) References Cited

U.S. PATENT DOCUMENTS

| | | |
|---|---|---|
| 5,528,658 A | 6/1996 | Hell |
| 5,841,829 A | 11/1998 | Dolazza |
| 5,872,828 A | 2/1999 | Niklason |
| 6,256,369 B1 | 7/2001 | Lai |
| 6,542,575 B1 | 4/2003 | Schubert |
| 6,553,096 B1 | 4/2003 | Zhou et al. |
| 6,895,076 B2 | 5/2005 | Halsmer |
| 6,940,943 B2 | 9/2005 | Claus |
| 6,950,492 B2 | 9/2005 | Besson |
| 6,950,493 B2 | 9/2005 | Besson |
| 7,001,071 B2 | 2/2006 | Deuringer |
| 7,016,461 B2 | 3/2006 | Rotondo |
| 7,110,490 B2 | 9/2006 | Eberhard |
| 7,190,758 B2 | 3/2007 | Hagiwara |
| 7,244,063 B2 | 7/2007 | Eberhard |
| 7,286,645 B2 | 10/2007 | Freudenberger |
| 7,319,736 B2 | 1/2008 | Rotondo |
| 7,356,113 B2 | 4/2008 | Wu |
| 7,616,731 B2 | 11/2009 | Pack |
| 7,839,979 B2 | 11/2010 | Hauttmann |
| 7,885,384 B2 | 2/2011 | Mannar |
| 8,031,834 B2 | 10/2011 | Ludwig |
| 8,457,282 B2 * | 6/2013 | Baorui et al. ............ 378/137 |
| 2002/0126798 A1 | 9/2002 | Harris |
| 2003/0058989 A1 | 3/2003 | Rotondo |
| 2004/0109529 A1 | 6/2004 | Eberhard |
| 2004/0190682 A1 | 9/2004 | Deuringer |
| 2004/0247081 A1 | 12/2004 | Halsmer |
| 2004/0264627 A1 | 12/2004 | Besson |
| 2005/0025278 A1 | 2/2005 | Hagiwara |
| 2005/0113681 A1 | 5/2005 | DeFreitas |
| 2005/0133706 A1 | 6/2005 | Eberhard |
| 2006/0034426 A1 | 2/2006 | Freudenberger |
| 2006/0126780 A1 | 6/2006 | Rotondo |
| 2008/0056436 A1 | 3/2008 | Pack |
| 2008/0285712 A1 | 11/2008 | Kopans |
| 2010/0020937 A1 | 1/2010 | Hautmann |
| 2010/0020938 A1 | 1/2010 | Koch |
| 2010/0189227 A1 | 7/2010 | Mannar |
| 2010/0303202 A1 | 12/2010 | Ren |
| 2011/0026667 A1 | 2/2011 | Poorter |
| 2011/0188624 A1 | 8/2011 | Ren |
| 2012/0033868 A1 | 2/2012 | Ren |

FOREIGN PATENT DOCUMENTS

| | | |
|---|---|---|
| WO | WO2007129244 | 11/2007 |
| WO | WO2008072144 A1 | 6/2008 |
| WO | WO2009122328 A1 | 10/2009 |
| WO | WO2009136349 | 11/2009 |

OTHER PUBLICATIONS

Kachelriess, 2004 IEEE Nuclear Science Symposium Conference Record, Oct. 16-22, 2004, Rome Italy, vol. 6, pp. 3759-3763.

* cited by examiner

TOMOSYNTHESIS WITH SHIFTING FOCAL SPOT AND OSCILLATING COLLIMATOR BLADES

CROSS-REFERENCE TO RELATED APPLICATIONS

This application is a continuation application of U.S. patent application Ser. No. 12/849,294 filed Aug. 3, 2010, which is a continuation-in-part of U.S. patent application Ser. No. 12/623,472 filed Nov. 23, 2009, which claims priority to U.S. Patent Provisional Application Ser. No. 61/117,453 filed Nov. 24, 2008, all of which are incorporated by reference herein.

BACKGROUND OF THE INVENTION

Breast tomosynthesis is a three-dimensional imaging technology in which images of a stationary compressed breast are acquired at multiple angles during a short scan. The images are organized as a series of thin high-resolution slices that can be displayed individually or in a dynamic ciné mode. Breast tomosynthesis systems are similar to mammography systems except that the x-ray source is moved to a variety of different imaging positions during image acquisition. Reconstructed tomosynthesis slices advantageously reduce or eliminate problems caused by tissue overlap and structure noise in single slice two-dimensional mammography imaging. Digital tomosynthesis, which combines digital image capture and processing with simple tube/detector motion as used in computed tomography (CT) but over a smaller rotational angle than that used in CT, offers the additional possible advantages of reduced breast compression, improved diagnostic and screening accuracy, fewer recalls, and 3D lesion localization. However, movement of the x-ray source introduces some technological complications.

Typical tomosynthesis systems are arranged to smoothly and continuously traverse a path during an image scan because stop-and-start scanning procedures tend to reduce image quality. The x-ray source is activated for an exposure time of about 10 ms to 100 ms as the x-ray source moves into each of several imaging locations in the imaging path, and exposure is repeated with a cycle period of 200 ms to 2 seconds. After each exposure the x-ray source is deactivated. As the x-ray source moves between imaging locations the contents of the digital image detector are read out and stored. There is a minimum time period associated with reading the image from the digital detector, and the overall speed of the tomosynthesis scan is determined by the minimum time period for detector read, the exposure time at each location and the number of exposures. As the x-ray source is continuously moved through space during each exposure period in a tomosynthesis system the focal spot also moves. The resultant focal spot movement causes image blurring and reduces diagnostic accuracy.

SUMMARY OF THE INVENTION

In accordance with one aspect of the invention, an apparatus comprises: an x-ray source which defines a static focal spot; a collimator which controls the dispersion of radiation from the x-ray source; a detector which obtains images while the x-ray source is in motion; and a motion controller which synchronizes movement of the static focal spot, x-ray source and collimator such that the static focal spot and collimators are moved in a direction opposite to directional movement of the x-ray source during an exposure period.

In accordance with another aspect of the invention, a method comprises: performing a tomosynthesis scan including synchronizing movement of a static focal spot, x-ray source and collimator using a motion controller, including moving the static focal spot and collimator in a direction opposite to directional movement of an x-ray source during an exposure period.

DETAILED DESCRIPTION

Figure 1:
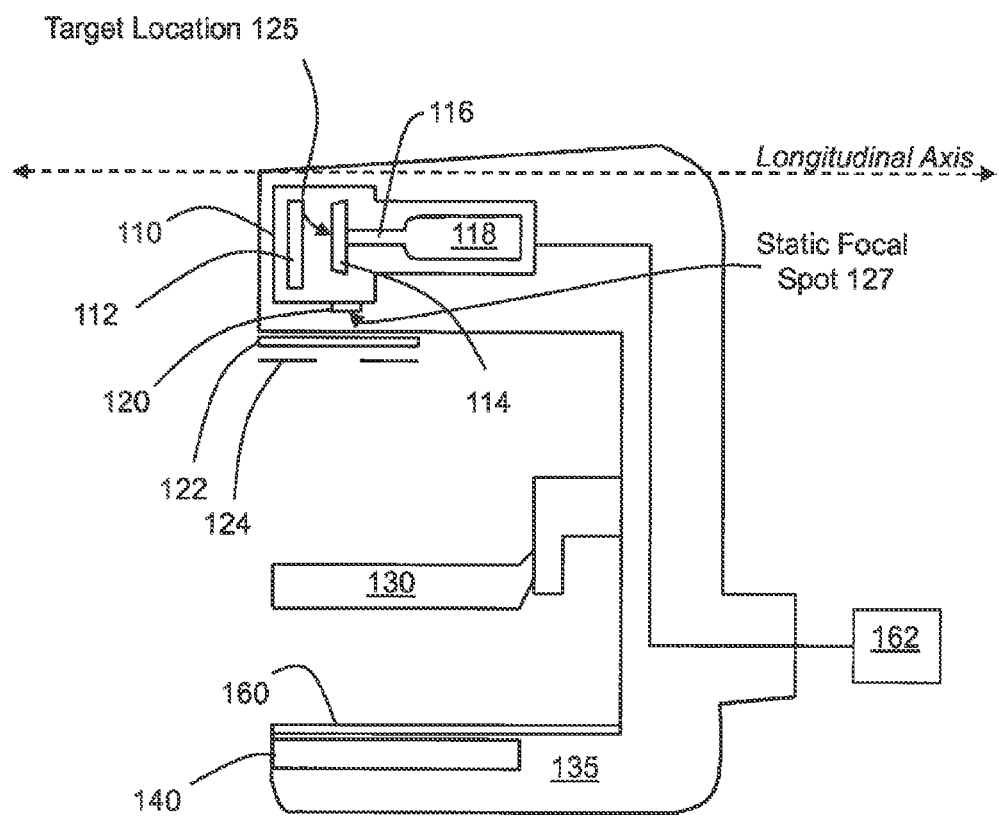
FIG. 1 illustrates a breast tomosynthesis system.

FIG. 1 illustrates a tomosynthesis system 100 which includes an x-ray tube 110, upper and lower compression paddles 130, 135, an anti-scatter grid 140 and a detector 160. The x-ray tube 110 includes a cathode 112, an anode 114 that is mounted on a shaft 116 and rotated by a motor 118, and a tube port 120. Also shown attached to the x-ray tube are a filter 122 and collimating means such as collimator blades 124.

The illustrated x-ray tube is a glass vacuum tube. Within the cathode 112 is a heated filament. When the x-ray tube is turned 'on,' a current is passed through the filament, thereby heating the filament and causing high energy electrons to be dislodged from the filament. A high voltage between cathode and anode causes the electrons to accelerate toward a target location 125 on the anode. The anode is made, for example, from tungsten and is rotated by motor 118 to avoid local overheating of the target location 125 on the anode. Electrons are focused to a specific target location by means of a focusing cup (not shown) which is a separate control electrode that is cylindrical in shape and attached to the cathode, partially surrounding a filament of the cathode. The dislodged electrons collide with the tungsten atoms of the anode and x-ray photons are generated having bremsstrahlung radiation and characteristic line emission spectra. The x-ray photons are emitted in all directions from the target location 125.

The x-ray photons which come out of the tube port 120 are used for imaging. For the purposes of this application, the x-ray photons which come out of the tube port define a static focal spot 127. The static focal spot 127 is the focal spot as it appears from directly beneath the x-ray tube from the perspective of the breast, at or near the chestwall position of the patient. Focal spot characteristics are defined by International Standard CEI IEC 60336. Generally, the focal spot is rectangular in shape and stated for two normal directions of evaluation referred to as the length and width direction. The length direction is generally parallel to a longitudinal axis of the x-ray system, and the width direction is generally perpendicular to the longitudinal axis. The longitudinal axis of an exemplary tomosynthesis system is shown in FIG. 1.

Static focal spot size refers to the focal spot size at any given instantaneous moment in time, as compared to the time-averaged focal spot size during an x-ray exposure of finite time period which is referred to herein as the effective focal spot size of an x-ray exposure. The size of the static focal spot 127 significantly affects the heat loading capacity of the x-ray tube. Greater heat loading is possible with larger focal spots, thereby allowing a higher tube current mA to be safely provided. The size of the focal spot is determined by a combination of factors including the size and shape of the filament and the shape and bias voltage of the focusing cup. The angle of the target surface further defines a focal spot size along the so-called length direction.

The size of the focal spot is an important factor in a diagnostic x-ray tube because it affects the resolution of the radiography system. More particularly, systems having smaller focal spots have better resolution, so reducing static focal spot size is one design goal. For example, mammography systems may be designed to provide a 0.3 mm focal spot for imaging (0.1 mm focal spot for high magnification images). Movement of the x-ray source during image exposure effectively stretches the width of the static focal spot, resulting in an effective focal spot which is wider than the static focal spot and which decreases image sharpness. The size of the effective focal spot is therefore determined by the size of the static focal spot and the motion of the static focal spot during exposure, and the effective focal spot (aka dynamic focal spot) is the accumulation of the static focal spot over time.

Figure 2:
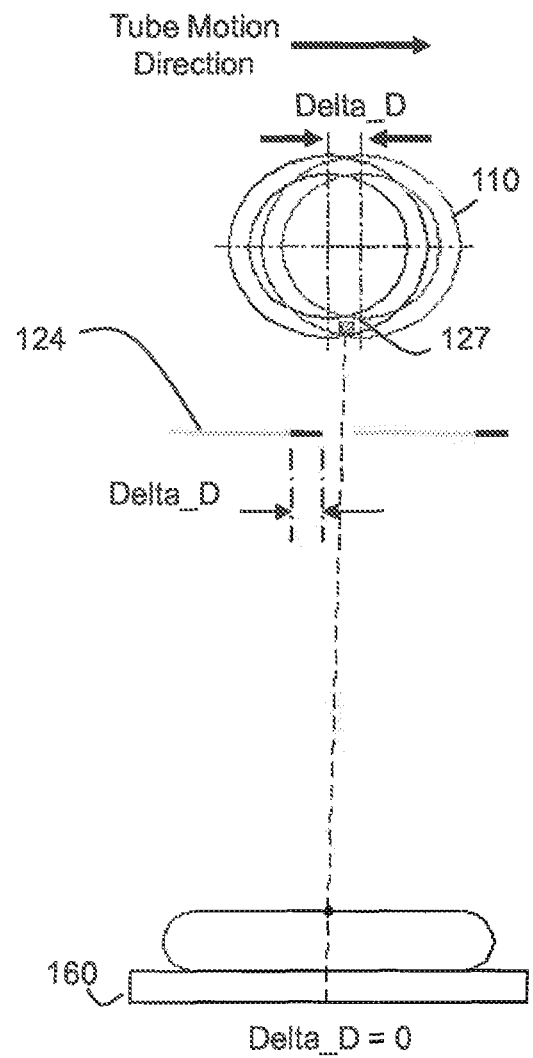
FIGS. 2 and 3 illustrate synchronized movement of the static focal spot, x-ray tube and collimator blades.
Figure 3:
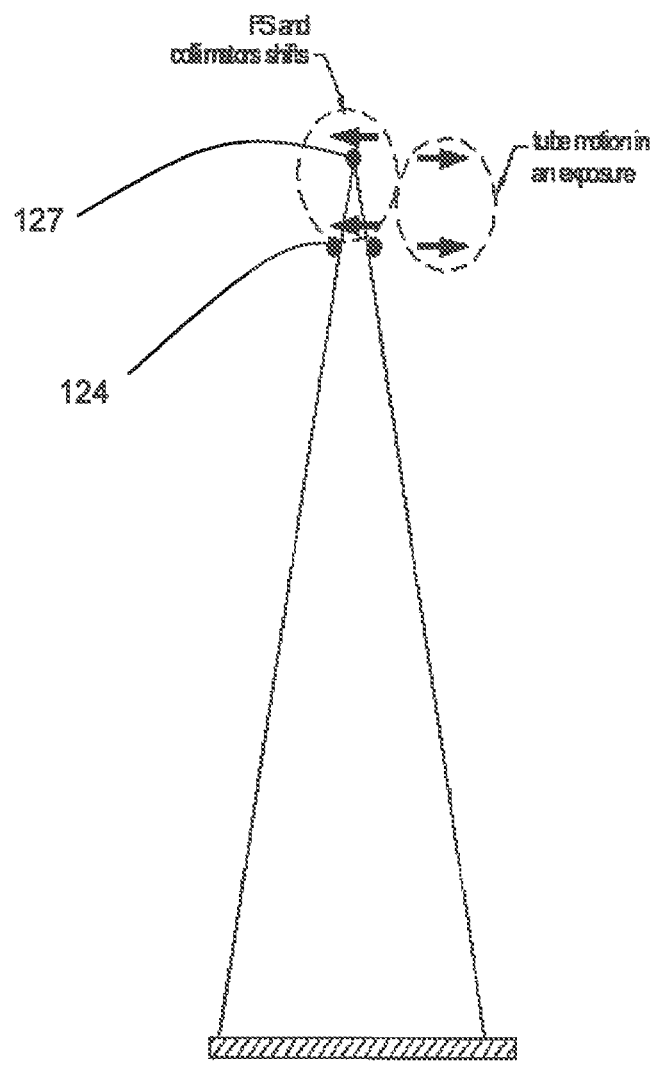

As illustrated in FIGS. 2 and 3, the static focal spot is moved at the same linear speed in a direction opposite to and generally synchronized with the directional movement of the x-ray source during the exposure period. Further, the x-ray collimator blades 124 are moved during each exposure in synchronization with the movement of the static focal spot to keep the collimated rays contained within a boundary as governed by FDA field limitation compliance regulation. The synchronized movement of the static focal spot, x-ray tube and collimator blades helps keep the effective focal spot fixed in space relative to the breast for the entire duration of the exposure and keeps the x-ray field on the detector and breast static.

The focal spot and shifting collimator blades follow a linear oscillating pattern over the multiple x-ray exposures of a tomosynthesis scan. Before an exposure the focal spot and collimator blades are moved to start positions. The collimator blades then shift following the motion of the static focal spot during the exposure. At the end of exposure the focal spot and collimator blades are moved back to the start positions to prepare for the next exposure. This process is repeated until all x-ray exposures are finished in a scan. When the scan is complete the focal spot and collimator blades are set to a center position, which is the position for conventional imaging.

Figure 4:
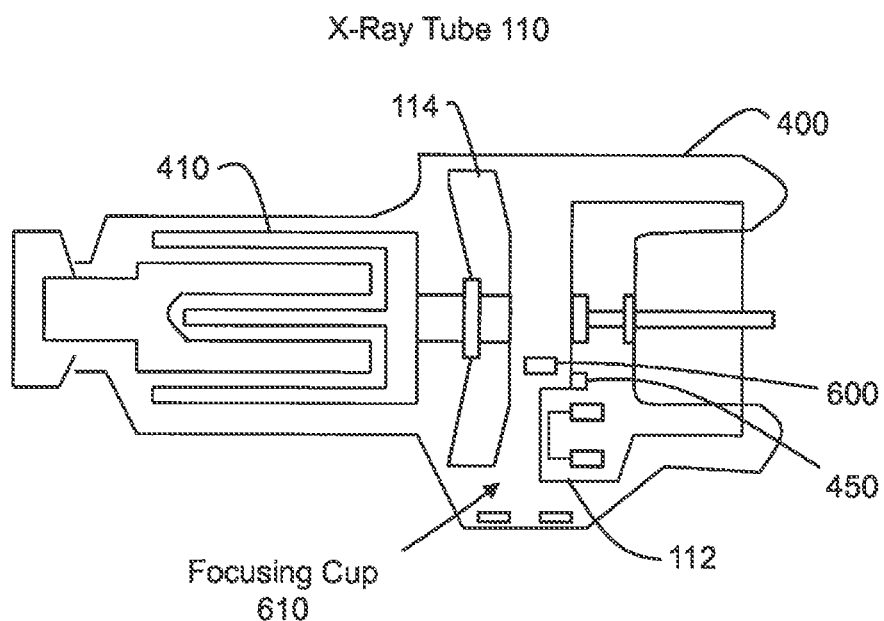
FIG. 4 illustrates an x-ray tube with a focal spot and collimator blade position controller.

FIG. 4 illustrates an x-ray tube 110 including a vacuum tube 400 which encases an anode 114, a cathode 112 and an anode rotor 410. The collimator blades and tube (c'arm) each have closed loop controllers which are calibrated for positional accuracy. A main processor 162 (FIG. 1) equipped with memory for storing program code regulates the motion synchronicity of the focal spot, collimator blades and tube (c'arm). According to one aspect of the invention, the x-ray tube further includes a focal spot and collimator position controller 600. The controller may be coupled to the cathode 112 to deflect the electron trajectory in the 'width' direction. In its simplest form the controller comprises two parallel metal plates located next to the focusing cup 610, with a bias voltage applied across the plates that can shift electron motion direction, and therefore the target location on the anode. Focal spot displacement is proportional to the bias voltage level applied by a voltage controller 450. The shift of the focal spot is therefore controlled via an application of a bias voltage across the plates. In several embodiments, the bias voltage can be dynamically or statically configured prior to x-ray exposure.

Figure 5:
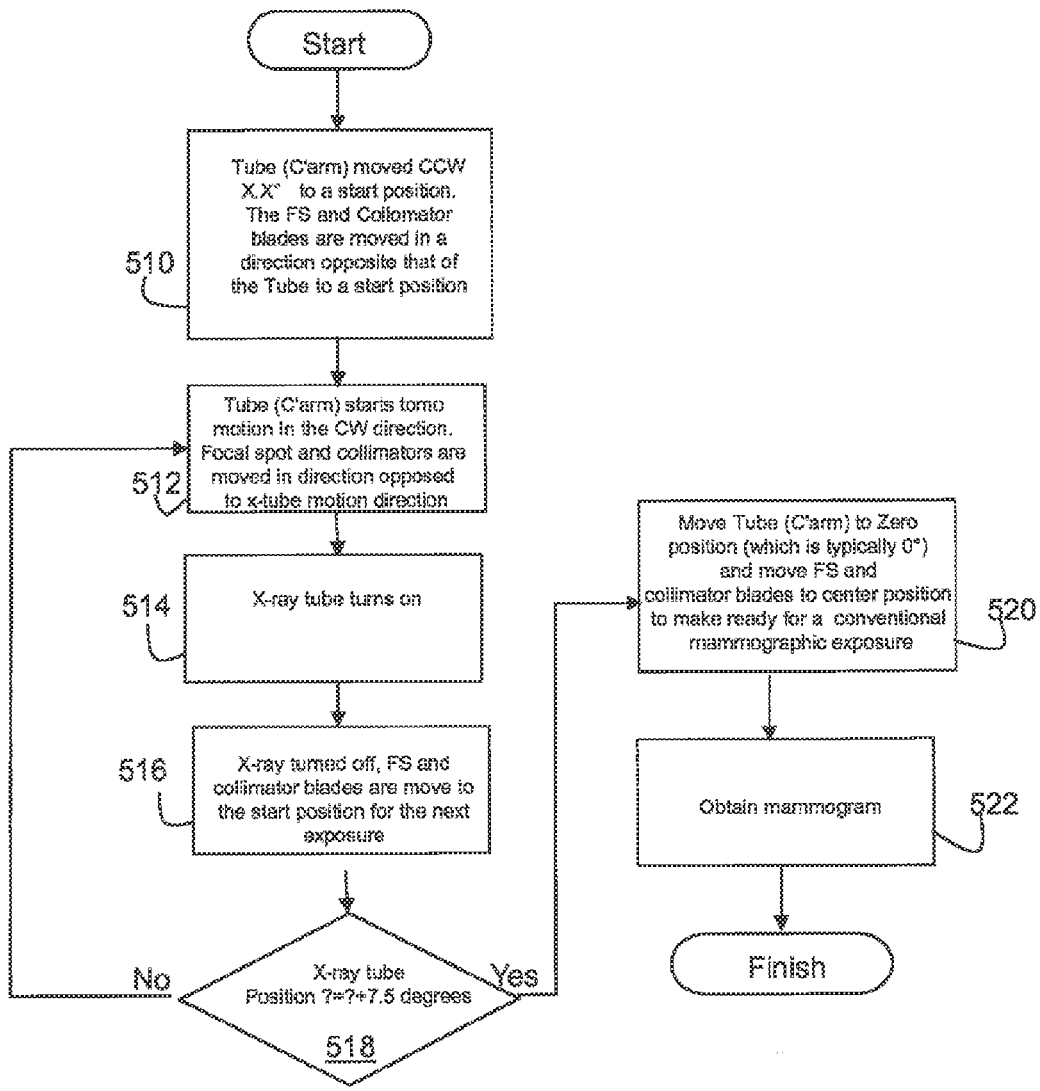
FIG. 5 illustrates a process of using a tomosynthesis system for 2D and 3D imaging.

Referring now to FIG. 5, a process of using a tomosynthesis system for 2D and 3D imaging will now be described. At step 510 the tube (C'arm) is moved CCW (counter clockwise) X.X° to a start position. The focal spot and collimators blades are moved in a direction opposite that of the tube to a start position. As indicated by step 512, the tube (C'arm) starts tomosynthesis motion in the CW (clock-wise) direction and the static focal spot is moved in a direction opposite to and generally synchronized with the directional movement of the x-ray source, and the x-ray collimator blades are moved in synchronization with the shifting of the static focal spot. Although illustrated as a step in the process it will be appreciated that these synchronized movements are continuous over the duration of the exposure. The x-ray tube is activated upon reaching an initial imaging position as illustrated by step 514. In one embodiment, each exposure takes less than 60 ms. During the exposure, the gantry continues to move towards the +7.5 degree position, and the x-ray tube focal spot motion controller sets the focal spot to a starting position on the anode which is pre-calculated based on the x-ray technique and gantry scan speed of the intended tomosynthesis scan, moves the static focal spot in the opposite direction (in this example, clockwise tomosynthesis scan). At step 516, when the exposure is complete and focal spot at the same time reaches the pre-calculated stop position, the x-ray tube is turned off and the static focal spot and collimator blades are moved to the start position for the next exposure. At step 518 it is determined whether the end point of the clock wise scan has been reached (gantry at the +7.5 degree position). If not, steps 512 through 516 are repeated until all tomosynthesis projection images are obtained. At step 520 the tube (C'arm) is moved to a zero position (which is typically 0°) and the focal spot and collimator blades are moved to a center position to prepare for a conventional mammographic exposure. If the focal spot size had been increased for tomosynthesis imaging, it is reduced to the range which provides desired mammogram resolution. At step 522 the image is obtained and the process is complete.

It should be noted that although the x-ray tube is described as being turned 'on' or 'off,' some systems have x-ray tubes that are continuously on during the scan, with image capture being controlled by capture of the x-rays at the detector at select 'exposure times' times during the scan. In such instances, it can be appreciated that the focal spot motion is synchronized to the exposure start and exposure end times, regardless of whether the x-ray tube is cycled or is continuously 'on.'

Although a system, method and process of the present invention has been shown and described to improve tomosynthesis image clarity by static or dynamic management of focal spot size and position during an x-ray exposure, it should be noted that the present invention is not limited for use to any particular imaging modality. Rather it is envisioned that the x-ray tubes and collimator blades of the present invention may have utility in any system which obtains images while an x-ray source is in motion. For example, computed tomography (CT) systems experience focal spot blurring. The modified x-ray tube and collimator blades of the present invention may advantageously be used with CT systems to reduce the FS blur, making the Modulation Transfer Function (MTF) across field of view isotropic. In a breast CT system, one benefit of such an improvement would be that the MTF at the breast edge would be as good as that in the breast center in the horizontal plane. Accordingly, the embodiments described above are intended to be examples and are not intended to be exhaustive or to unduly limit the claimed inventions. The examples are intended to describe principles that persons skilled in the art may use to practice the claimed inventions, using variations and modifications of the disclosed examples that are suited to a particular environment. It is intended that the scope of the invention be defined by the appended claims and their equivalents.

What is claimed is:

1. A system for tomosynthesis imaging comprising:
an x-ray source configured to move to different imaging positions during tomosynthesis image acquisition;
a detector configured to obtain images while the x-ray source is in motion; and
a collimator configured to control dispersion of radiation from the x-ray source, the collimator being positionable so that the collimator moves in a direction opposite to the directional movement of the x-ray source during tomosynthesis image acquisition.

2. The system of claim 1, wherein the collimator comprises two blades, one blade spaced apart from a second blade.

3. The system of claim 2, wherein a distance between the two blades is constant even when the collimator moves during tomosynthesis image acquisition.

4. The system of claim 1, wherein the collimator moves to different positions relative to the x-ray source, the collimator positioned at a start position before an exposure period, the collimator moves in the direction opposite to the directional movement of the x-ray source during the exposure period, and the collimator positioned back at the start position after the exposure period.

5. The system of claim 4, wherein the collimator is positioned at a center position when the tomosynthesis image acquisition is complete.

6. The system of claim 4, wherein the system is also configured to obtain conventional 2D mammographic images, the collimator positioned at a center position to obtain the conventional 2D mammographic images.

7. The system of claim 1 further comprising a motion controller to synchronize movement of the x-ray source and the collimator.

8. The system of claim 7 further comprising a main processor to regulate the movement of the collimator and the x-ray source.

9. The system of claim 1, wherein the collimator and the x-ray source each have closed loop controllers.

10. The system of claim 1 further comprising a collimator position controller configured to control the position of the collimator.

11. The system of claim 10, wherein the collimator position controller comprises two parallel metal plates located next to a focusing cup, which focuses electrons of the x-ray source to a specific target location.

12. The system of claim 1, wherein the x-ray source defines a static focal spot and the static focal spot moves in a direction opposite to directional movement of the x-ray source during tomosynthesis image acquisition.

13. The system of claim 12, wherein the static focal spot is moved at a linear speed equal to that of the x-ray source during an exposure period.

14. The system of claim 12, wherein the static focal spot and the collimator follow a linear oscillating pattern over multiple x-ray exposures during tomosynthesis image acquisition.

15. The system of claim 12, wherein static focal spot displacement is proportional to a bias voltage level applied by a voltage controller.

16. The system of claim 15, wherein the bias voltage is dynamically or statically configured prior to an exposure period.

17. The system of claim 12, wherein the static focal spot moves to different positions relative to the x-ray source, the static focal spot positioned at a start position before an exposure period, the static focal spot moves in the direction opposite to the directional movement of the x-ray source during the exposure period, and the static focal spot positioned back at the start position after the exposure period.

18. The system of claim 17, wherein the static focal spot is positioned at a center position when the tomosynthesis image acquisition is complete.

19. The system of claim 17, wherein the system is also configured to obtain conventional 2D mammographic images, the static focal spot positioned at a center position to obtain the conventional 2D mammographic images.

* * * * *